(12) United States Patent
Draenert et al.

(10) Patent No.: US 6,723,130 B2
(45) Date of Patent: Apr. 20, 2004

(54) NECK-PRESERVING-STEM NPS

(76) Inventors: Klaus Draenert, Gabriel Max Strasse 3, D-81545 Munich (DE); Klaus Blaesius, Auf dem Koenigreich 8, D-52224 Stolberg (DE)

( * ) Notice: Subject to any disclaimer, the term of this patent is extended or adjusted under 35 U.S.C. 154(b) by 0 days.

(21) Appl. No.: 09/919,178

(22) Filed: Jul. 30, 2001

(65) Prior Publication Data

US 2003/0171821 A1 Sep. 11, 2003

(30) Foreign Application Priority Data

Jul. 29, 2000 (DE) .......................... 100 36 986

(51) Int. Cl.$^7$ .................................. A61F 2/36
(52) U.S. Cl. .................. 623/23.35; 623/23.15
(58) Field of Search ................ 623/22.11, 22.4, 623/22.41–22.46, 23.15, 23.19, 23.24, 23.31, 23.35

(56) References Cited

U.S. PATENT DOCUMENTS 5,358,534 A * 10/1994 Dudasik et al. .......... 623/23.35
5,888,210 A * 3/1999 Draenert .................. 623/23.35

* cited by examiner

*Primary Examiner*—Corrine McDermott
*Assistant Examiner*—Thomas C. Barrett
(74) *Attorney, Agent, or Firm*—Westman, Champlin & Kelly, P.A.

(57) ABSTRACT

The present invention essentially relates to a hip joint endoprosthesis stem for cement-free or cemented anchoring in bones that is anchored in the femoral neck and in the proximal metaphysis and preserves the internal spongiosa and compact structures that reinforce the femur, that gives the design element axial access to the medullary canal, and possesses parabolically curved outer surfaces to optimize the transfer of force to the bone.

7 Claims, 4 Drawing Sheets

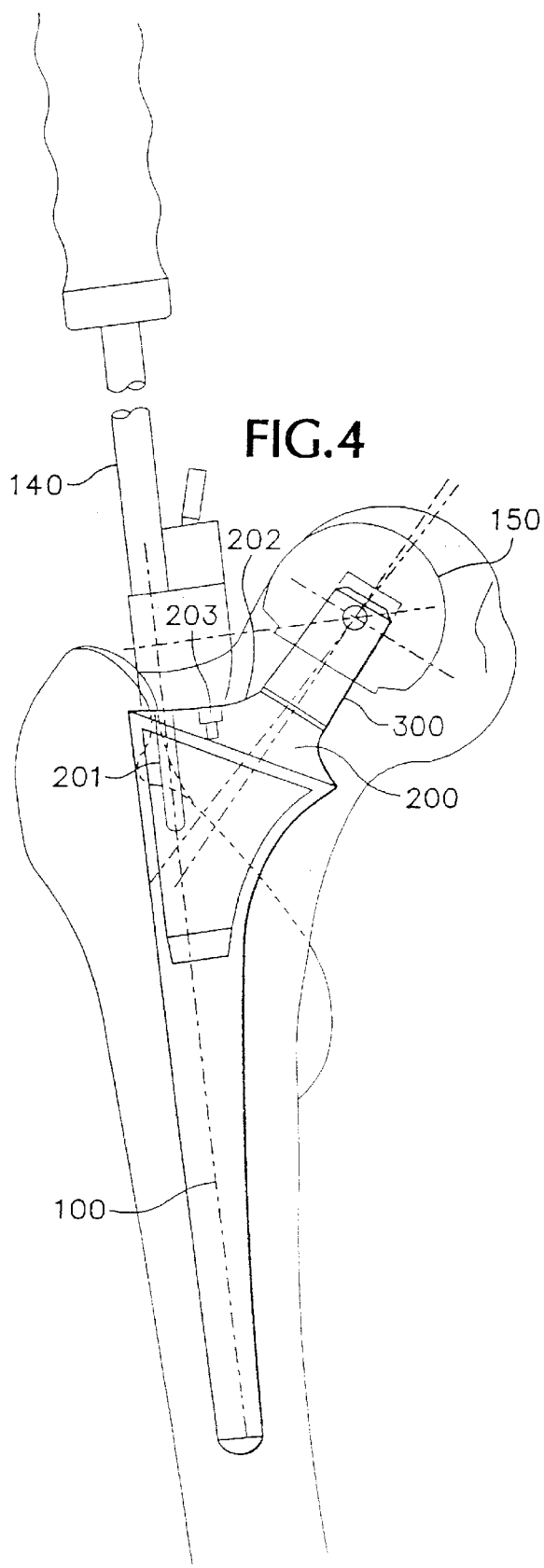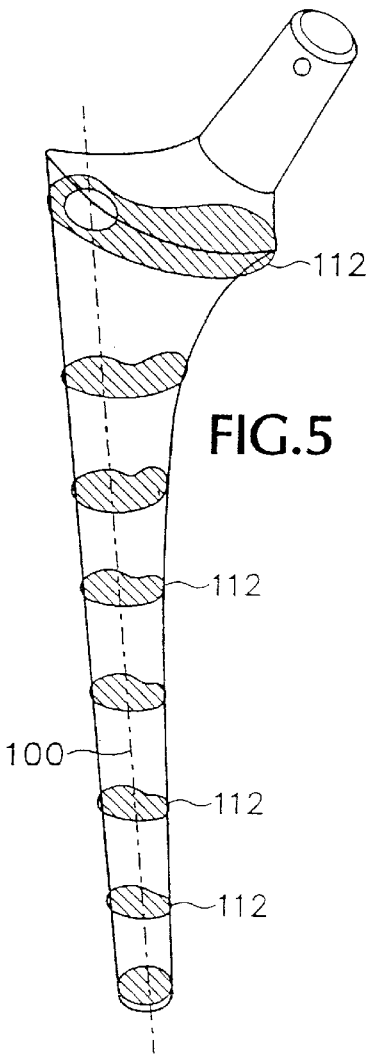

NECK-PRESERVING-STEM NPS

BACKGROUND OF THE INVENTION

The present invention relates to a hip prosthesis that has a femoral component including a stem shaped with a parabolic outer surface and a straight dorsal indentation that extends in a straight line along its length, but has different depths. When inserted into the femoral canal it provides optimal transfer of forces to the bone. Anatomically, there is little correlation between the morphology of the diaphysis and the structure of and loads on the metaphysis. However, the physiological laws of force transfer that dictate that the bone will be most strongly reinforced at the locations where the strongest loads are encountered do apply. The loading of the bone is reflected in its structure. These principles can be used in designing a prosthesis, in particular in taking the prosthesis interface into account. It has been found that the best long-term results are not obtained with a prosthesis that most closely duplicates the compact exterior geometry of the bone (custom-made prostheses), but rather with one that possessed the reinforcing structures of the bone in an optimal manner (Draenert, K., et al., 1999, *Manual of Cementing Technique*, Berlin, Heidelberg: Springer). The object of this invention is to provide the reinforcing structures in the proximal femur, to apply the load to the bone proximally, and to achieve a maximum degree of rotational stability.

The design of conventional stems of femural components tends to duplicate the frontal projection of the femur. This is true both for cemented components and for uncemented anchored designs: see Charnley, J., (1960), Anchorage of the Femural Head Prosthesis to the Shaft of the Femur, *J. Bone and Joint Surg.* B42: 28–30, or also Zweymüller, K. A., et al., (1988), Biologic Fixation of a Press-Fit Titanium Hip Joint Endoprosthesis, *Clin. Orthop.* 235: 195–206. However, it has been found that a substantial torque load results when the heel strikes the ground, when the patient climbs stairs, or, in general, when the hip joint is extended from the flexed position. If one studies the phylogenetic and ontogenetic development of the femoral neck, it becomes clear that this "heel-strike phase" causes a large retrotorsional moment to be applied to the neck of the femur. The design of the prosthesis must take this torque into account.

Thus far, success in applying the force proximally to the metaphysis has only been achieved by using bone cement, as described in Draenert, K., and Draenert, Y., 1992, *Forschung und Fortbildung in der Chirurgie des Bewegungsapparates* 3: *Die Adaption des Knochens an die Deformation durch Implantate* [Research and Advances in Locomotor System Surgery 3: Using Implants to Adapt the Bone to Deformations], Munich: Art and Science. In 1986, M. A. R. Freeman asked why the neck of the femur should be resected (Freeman, M. A. R., 1986, Why Resect the Neck?, *J. Bone Joint Surg.*, 68B: 346–349); increased rotational stability was discussed but not implemented in the design, since the importance of the anatomical structures had not yet been recognized. Thus, the resulting stem was straight and did not exhibit right-left symmetry.

However, it was found that it was precisely the anatomical structures of the proximal femur that were responsible for the bone's rigidity, torsional strength, and ability to withstand high flexural loads. Thus, all of the anatomical structures, right down to the finest structural reinforcement provided by the spongiosa, need to be provided in the highly integrated overall design.

SUMMARY OF THE INVENTION

The present invention relates to a uniquely configured stem for a femoral insert of a hip prosthesis. The stem has a parabolic outer surface at its proximal end and a dorsal indentation that is straight along the length of the stem. The dorsal indentation changes in depth along the stem length with the deepest indentation at the proximal end. The configuration optimizes the transfer of force from the prosthesis to the bone.

BRIEF DESCRIPTION OF THE DRAWINGS

FIG. 4 is a view illustrating an installation tool engaging the prosthesis;

FIG. 5 is a view of the prosthesis showing a cross-sectional configuration of the stem at different positions on the stem.

DESCRIPTION OF THE PREFERRED EMBODIMENTS

Figure 1:
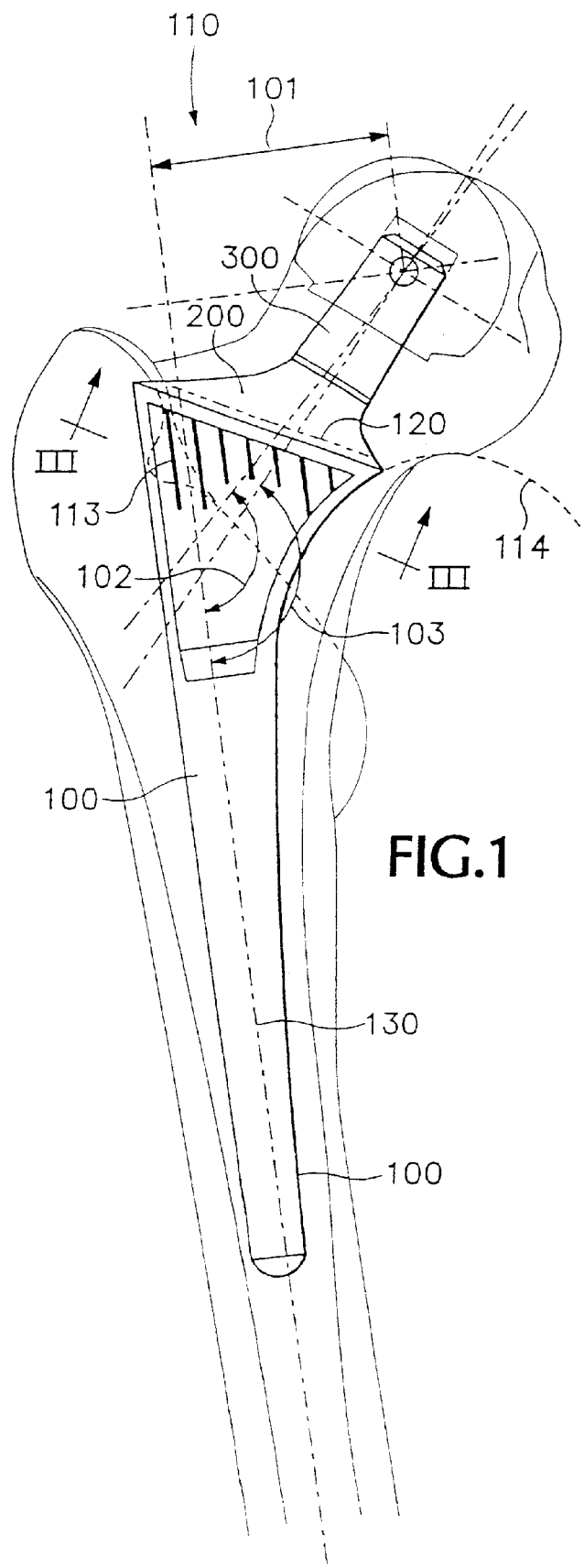
FIG. 1 is an anterior view of a prosthesis made according to the present invention.

One of the substantive elements of the prosthesis stem is the straight-line opening of the medullary canal through the greater trochanter (FIG. 01/110). The entire neck of the femur (FIG. 01/120) is preserved through the osteotomy. The design of the stem (FIG. 01/100) allows it to be inserted in a straight line, provided that a guide instrument in the opening canal can be inserted into the medullary canal without encountering resistance. This is the case when the opening has been executed correctly along the dorsal wall of the neck in a straight extension of the canal axis through the greater trochanter. The dorsal wall of the neck forms a straight line with the dorsal wall of the medullary canal.

Figure 2A:
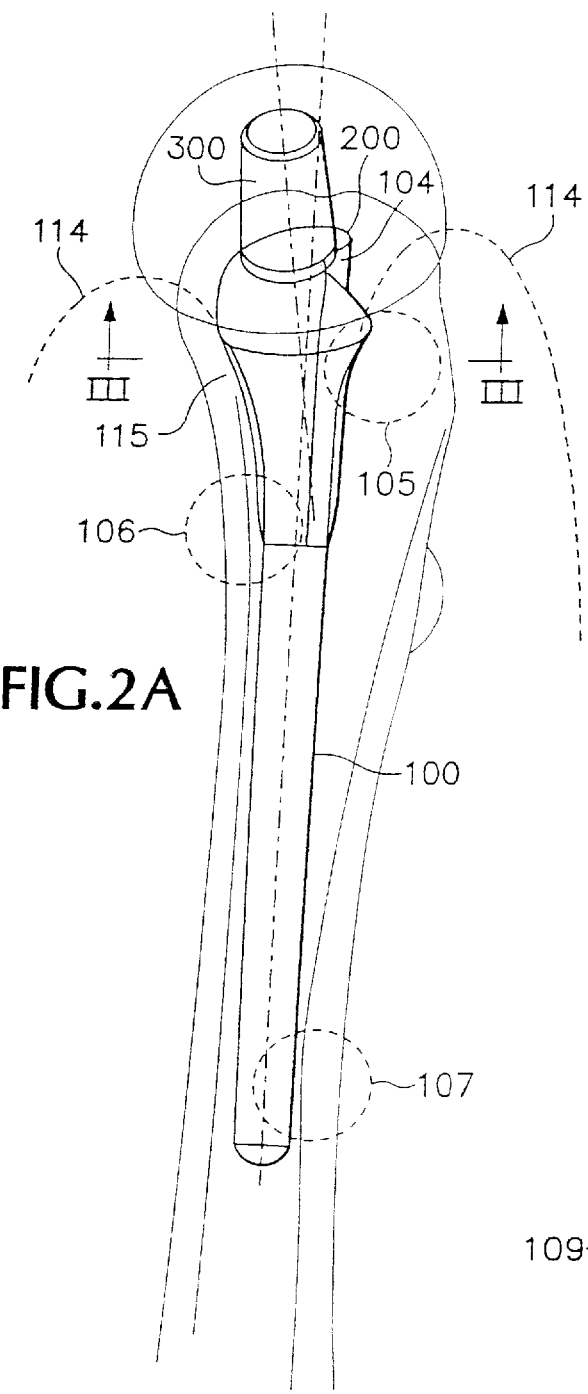
FIG. 2A is a medial view of the prosthesis of FIG. 1.
Figure 2B:
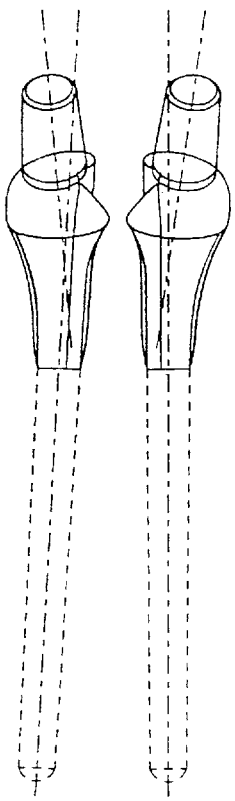
FIG. 2B is a showing of left-right symmetry of the prosthesis.

The design of the prosthesis takes this anatomy into account and utilizes a cylinder (FIG. 03/109) as a design element located around the canal axis (FIG. 01/130) around which the stem is designed to coincide with the anatomical clearances (FIG. 02.1), which results in symmetrically opposite right-left versions (FIG. 02.2).

This results in a symmetrically opposite cross section (FIG. 03), which has as its most striking element a flat to deep indentation that is located along the dorsal side of the stem (FIG. 03/104) and that extends in a straight line into the tip of the prosthesis.

Figure 3:
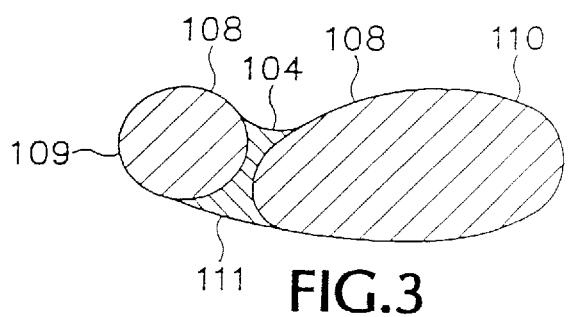
FIG. 3 is a sectional view taken on line III—III of FIG. 2A.

This basically produces a convex-concave-convex curve (FIG. 03/109—FIG. 03/104—FIG. 03/110)=S-shaped curve (FIG. 03/108).

The reconstruction of the center of rotation takes two parameters into account: First, it was found that there is a close relationship between the so-called metaphysis opening plane (Draenert et al., 1999, *Manual of Cementing Technique*, Berlin, Heidelberg: Springer) and the center of rotation (RZ), namely that the center of rotation is, as a rule, located 25 mm above this plane. Second, it was found that a prosthesis offset—the distance from the design axis or canal axis to the center of rotation of the head of the femur—of 45 mm was too long (Charnley, J., 1989, *Low*

*Friction Arthroplasty of the Hip: Theory and Practice*, Berlin, Heidelberg, New York: Springer). Based on clinical experience, a lever arm having a 40-mm offset was considered to the optimal. The design is based on this figure (FIG. 01/101).

This clinical experience also teaches that a physiological center-collum-diaphysis angle of 126° causes long-term anchorages to experience an increased failure rate. An angle of 135° (FIG. 01/102) has proven to be effective over many years, since the force is applied to the tubular portion of the femur bone as a direct compression load. One of the unique characteristics of this prosthesis is that the axis of the cone does not need to be identical to the CCD angle and instead can be steeper by 3° to 15°—as a rule, 5° to 6° (FIG. 01/103), in order to intensify this effect.

The length of the stem takes the S-shaped curve in the lateral projection into account. It ranges from 14 cm to 22 cm, and is generally about 15 cm in order to achieve reliable blocking between these curvatures (FIG. 0.2/105, FIG. 02.1/106, and FIG. 02.1/107).

The unique feature of this prosthesis is its straight-line, anatomically symmetrically opposite design: the outer dorsal surface has an undulating shape in the form of a rounded "3," the halves of which are uneven (FIG. 03/108). This divides the body of the prosthesis into a lateral cylindrical portion (FIG. 03/109) and a neck portion (FIG. 03/110) joined by connecting portion (FIG. 03/111). The dorsal indentation in the cross-section extends in a straight line along the entire length of the stem, although its depth decreases (FIG. 05/112). The cross sections are kidney-shaped but are not uniformly identical (FIG. 05/112).

Figure 6:
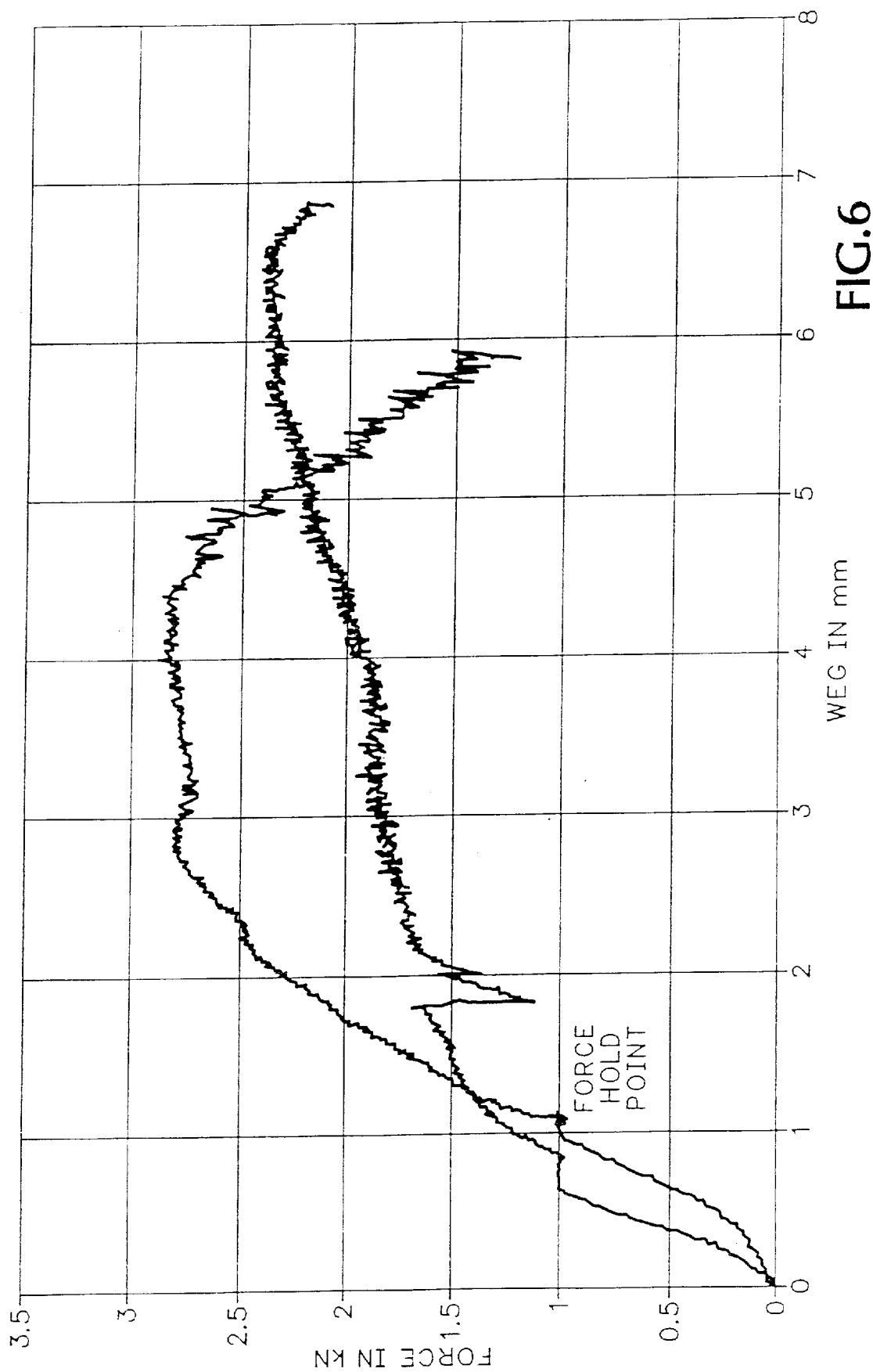
FIG. 6 is a load versus deflection diagram of two prosthesis stems with different outer surface curvatures.

The exterior surfaces are also structured to include coaxially aligned longitudinal grooves and ribs, generally in the ventral and dorsal positions. The design curvature is parabolic, resulting in a U-shaped force transfer (FIG. 02.1/114). This parabolic curve is superimposed on the bone structure (FIG. 02.1/115). The curvature of the exterior surfaces defines the load/deflection diagram in the load test (FIG. 06).

The insertion hole (FIG. 04/201) for positioning the insertion instrument (FIG. 04/140) is located on the extension of the axis, as is a corresponding abutment surface (FIG. 04/202) for the force fit or thread used to fix the position of the insertion instrument with trial prostheses (FIG. 04/203).

Both structures are located on the prosthesis shoulder (FIG. 04/200), which forms the transition to the cone (FIG. 04/300) that carries the variable head (FIG. 04/150).

EXAMPLE OF THE INVENTION

Once the hip joint has been exposed via the standard technique of dorsal or lateral access, the head of the femur is removed along the planned height while preserving the femoral neck and taking the respective metaphysis opening plane into account.

After the socket has been inserted the femur is positioned is such a way that the medullary cavity can be opened.

Along the extension of the medullary canal axis, the femur is opened at the "knee" of the greater trochanter using a 11.2-mm diameter (Dm) diamond hollow grinding wheel, and the straight guide instrument, having a diameter Dm of 11 mm and a tip that narrows to 6 mm, is inserted (FIG. 05).

The femoral metaphysis is then ground open using a hollow diamond-faced grinding wheel, and a trial prosthesis is mounted on the insertion instrument (FIG. 04). The tip of the trial prosthesis is carefully guided in via the opening hole, and then driven into the femur metaphysis via gentle hammering. If this is not possible, the medullary canal of the femur is ground open dorsally while carefully preserving the rear wall of the femoral neck, so that the cylindrical component of the stem fits in neatly behind the femoral neck.

The size of the prosthesis is measured in two ways: the guide instrument has a scale for measuring length that indicates the size of the prosthesis. The measuring instrument must be securely restrained in the S-shaped curve of the femur. The size can be read at the transition from the neck to the greater trochanter (FIG. 06). A sliding caliper can be used in the sagittal projection to determine the maximum diameter of the inner contour of the neck. The sliding caliper is also used to determine the size of the prosthesis.

The final prosthesis is driven in in the same fashion until it is anchored in the conical opening in the neck in such a way that it is absolutely tight and secure.

Then the prosthesis is repositioned using a trial head, and the luxation tendency is determined. If there is no risk of luxation, the final socket insert and the final head can be installed, whereupon the prosthesis is repositioned, and the work is documented using an imaging device. The muscles are then reattached layer by layer, and the wound is closed up.

What is claimed is:

1. An anatomical femur component of an artificial hip joint having a stem, the stem having a proximal end and being elongated along a longitudinal axis to a tip and having a dorsal side, a medial portion and a lateral portion;

the stem of the prosthesis having a concave indentation on the dorsal side that extends axially in a straight line from the proximal end to the tip of the stem, and wherein the dorsal side of the proximal end engages the bone structures of a neck of a femur in which the stem is placed from the greater trochanter to position adjacent a side of the femur opposite the greater trochanter;

the dorsal side concave indentation dividing the stem proximal end into the medial portion that flairs out from the stem in medial direction in a conical shape, and a lateral portion that is substantially cylindrical axially along the length of the stem;

the cross section of the stem having a basic "comma" shape on the proximal end.

2. The femur component of claim 1, wherein the dorsal indentation decreases in concave indentation from the proximal end to the tip.

3. The femur component of claim 1, wherein the proximal end has an outer surface at its proximal end that is parabolic on the dorsal side and on a ventral side of the stem.

4. The femur component of claim 3, wherein the medial portion has an outer surface that is concave along a medial contour, and that the outer surface center of curvature is medial and has a radius that decreases continuously in the proximal direction to form a parabolic shape.

5. The femur component of claim 4, wherein the stem has a lateral outer surface that is substantially straight and partially circular in cross section.

6. The femur component of claim 1, wherein the stem proximal end has an outer surface formed in the shape of a parabola on the dorsal side, on a medial side, and on a ventral side.

7. The femur component of claim 1, wherein the proximal end of the stem has a ventral surface that is axially convex, and on the ventral side has a concave curvature that is substantially parabolic.

* * * * *